United States Patent [19]

Wapner

[11] Patent Number: 4,911,698
[45] Date of Patent: Mar. 27, 1990

[54] "CLEAN-CATCH" INTRA-LABIA URINARY COLLECTION DEVICE

[75] Inventor: Herbert H. Wapner, Winnisquam, N.H.

[73] Assignee: Dale Medical Products, Inc., Plainville, Mass.

[21] Appl. No.: 192,244

[22] Filed: May 10, 1988

[51] Int. Cl.4 .............................................. A61F 5/44
[52] U.S. Cl. ..................... 604/329; 604/346; 604/354; 128/761; 4/144.3; 4/144.4
[58] Field of Search ............... 128/760, 761; 604/317, 604/327-331, 346-348, 354; 4/144.1-144.4

[56] References Cited

U.S. PATENT DOCUMENTS

| 2,490,969 | 12/1949 | Kinyon | 4/110 |
|---|---|---|---|
| 3,072,125 | 1/1963 | O'Brien | 128/295 |
| 3,432,866 | 3/1969 | Schwartz | 4/144.2 |
| 3,512,185 | 5/1970 | Ellis | 4/110 |
| 3,528,423 | 9/1970 | Lee | 4/144.3 |
| 3,583,388 | 6/1971 | Hovick | 128/761 |
| 3,613,122 | 10/1971 | Gross et al. | 4/110 |
| 3,815,581 | 6/1974 | Levin | 128/2 |
| 3,900,019 | 8/1975 | Logiadis | 128/2 |
| 3,995,329 | 12/1976 | Williams | 604/329 |
| 4,202,057 | 5/1980 | Ibarra | 128/761 |
| 4,496,355 | 1/1985 | Hall et al. | 604/327 |
| 4,568,339 | 2/1986 | Steer | 604/329 |
| 4,615,692 | 10/1986 | Giacalone et al. | 604/94 |

FOREIGN PATENT DOCUMENTS

| 0212212 | 7/1909 | Fed. Rep. of Germany | 4/144.3 |
|---|---|---|---|
| 0378760 | 10/1907 | France | 604/329 |
| 0996370 | 6/1965 | United Kingdom | 4/144.3 |
| 2090144 | 7/1982 | United Kingdom | 604/331 |

Primary Examiner—C. Fred Rosenbaum
Assistant Examiner—Adam J. Cermak
Attorney, Agent, or Firm—Wolf, Greenfield & Sacks

[57] ABSTRACT

An intra-labia urinary collection device for obtaining a "clean-catch" urine specimen. The device is a hollow, oval body of rigid plastic having an upper wall with a front recess and oval opening positionable for receiving uncontaminated urine from the urethral opening. The upper wall further includes opposing side and rear recesses which meet at a raised central plateau to form a closed projection which fits in the vaginal opening. The rear recess engages the vestibular tissue rearwardly of the vaginal opening to seal the device in position and prevent contamination of the urine specimen by bacteria, cells or fluids from the vagina or anus. An enlarged hollow chamber is formed by vertical sidewalls at the widest section of the body which allows the device to handle a high rate of urine flow without leakage.

10 Claims, 3 Drawing Sheets

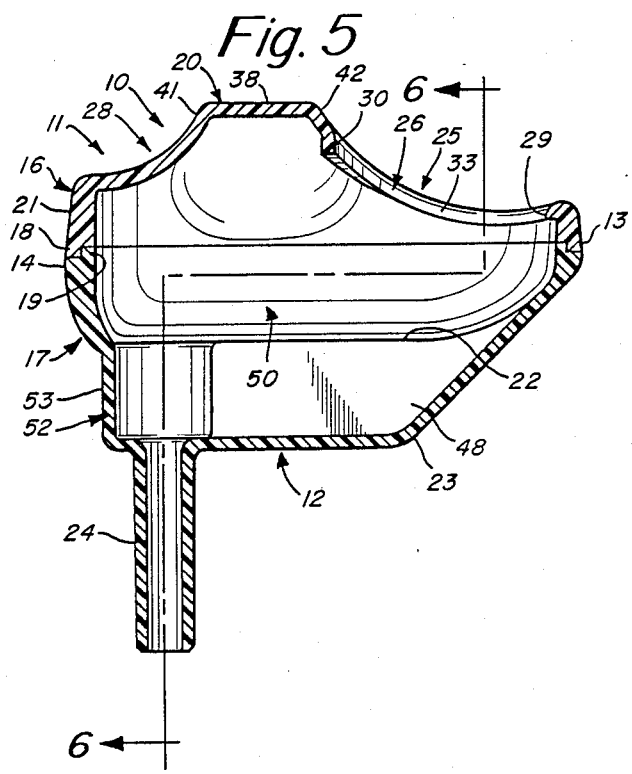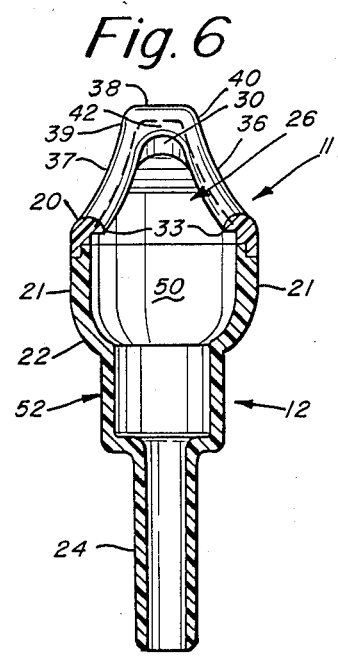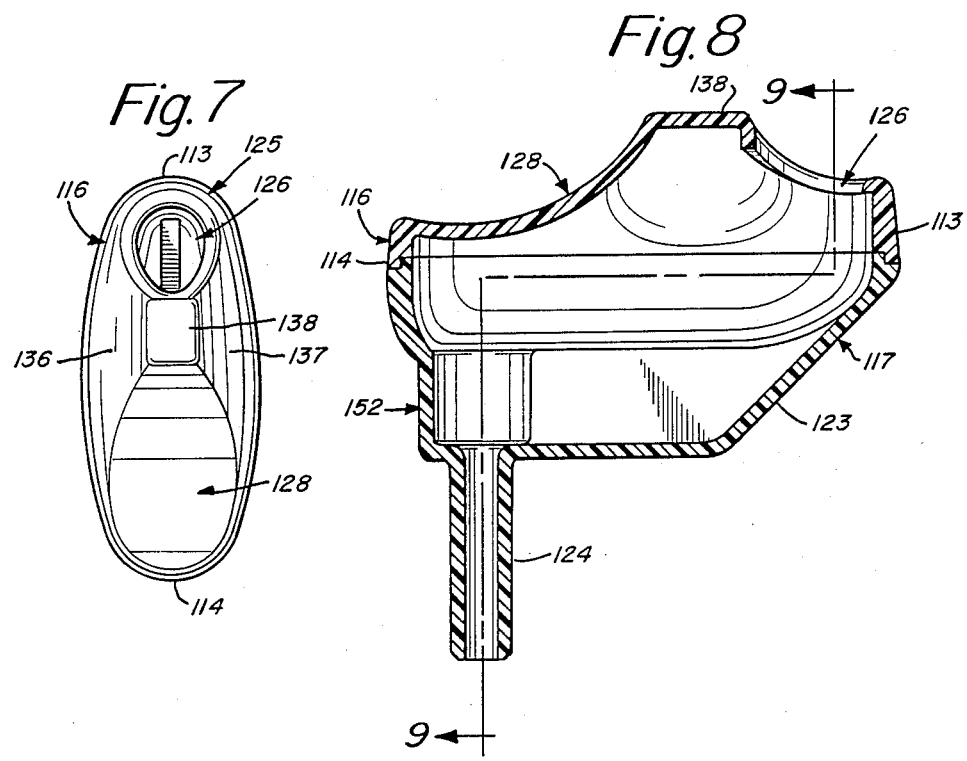

"CLEAN-CATCH" INTRA-LABIA URINARY COLLECTION DEVICE

BACKGROUND OF THE INVENTION

This invention relates to an intra-labia urinary collection device designed to obtain a "clean-catch" urinary sample free from contamination by bacteria or cells from the vagina.

Urinary tract infections are the second leading cause of physician visits in the United States. A urinary infection is typically caused by bacteria entering the discharge end of the urinary tract (the urethral opening) and traveling up the uretha (which carries urine from the bladder to outside the body). Women are more susceptible to the infection than men because their urethras are only about 1.5 inches long, compared with 8 or 9 inches in men. Furthermore, women's urethral openings are near anal and vaginal sources of infectious agents.

Diagnosing a urinary tract infection depends on analysis and culture of a "clean-catch" urine sample. A "clean-catch" specimen requires collecting the urine at midstream, since the first bit of urine may be contaminated with bacteria that has migrated into the urethra from the outside.

In a typical prior art procedure, a patient first wipes off the exterior genitalia, urinates a little into a toilet or bedpan and then, without interrupting the flow, urinates about an ounce more into a collection vial, finishing urinating into the toilet or bedpan if necessary. There is nothing to prevent contamination of the sample by bacteria or cells from the vagina or anus if the genital area has not been sufficiently cleaned, if there is a vaginal discharge after cleaning, or if urine enters the vagina during discharge.

The alternative to a simple vial collection has typically been a catheter inserted up the urethra and into the bladder. This may be painful and at least uncomfortable and many women greatly dislike this procedure.

There has thus long been a need for an external female urinary collection device for obtaining a clean-catch specimen for use in diagnosing a urinary tract infection. The device should ensure that the sample contains urine uncontaminated by fluids, bacteria or epithelial cells from either the vagina or anus. It is an object of this invention to provide such a device.

Another object of this invention is to provide an intra-labia urinary collection device for use by ambulatory or bedridden females who have the need to control or direct urine discharges when it is impractical or impossible to use a common urinal. Such persons must typically void urine in a supine position and it is desired that the urine drain easily and comfortably into the device with minimal if any leakage or spillage.

SUMMARY OF THE INVENTION

The apparatus of this invention is directed to an intra-labia urinary collection device for obtaining a clean-catch urine specimen. The device is also useful for voiding urine in either an upright or a supine position without leakage or spillage.

The device consists of an oval hollow body having narrowed and rounded front and rear ends and a wider middle section. The device is sized and configured to be substantially enfolded by the labia minora of the user and extend from just behind the clitoris to behind the vaginal opening.

An upper wall of the device includes, from front to back, a front concave recess, a raised projection, and a rear concave recess. Two side recesses are also provided on opposing sides of the projection. An oval opening having a wider front portion is provided in the front concave recess for receiving fluids from the urethral opening. The closed, raised projection having vertical sidewalls and an upper horizontal plateau is positionable in the vaginal opening to prevent vaginal fluids and cells from entering the body. The closed, rear concave recess is positionable against the vestibular tissue rearwardly of the vaginal opening for properly seating the device to prevent contamination of the urine collected in the body.

An enlarged chamber having vertical sidewalls extends the entire length of the body for collecting urine without leakage or spillage. A spigot extends downwardly from a lower wall of the body adjacent the rear end for funneling the urine to a depository.

BRIEF DESCRIPTION OF THE DRAWINGS

FIG. 5 is a side sectional view of the device of FIG. 1.

FIG. 6 is an end sectional view taken along the section lines 6—6 in FIG. 5.

FIG. 7 is a top plan view of a second embodiment of the intra-labia collection device of this invention for use by a child.

FIG. 8 is a side sectional view of the device of FIG. 7.

DETAILED DESCRIPTION OF THE PREFERRED EMBODIMENTS

Figure 1:
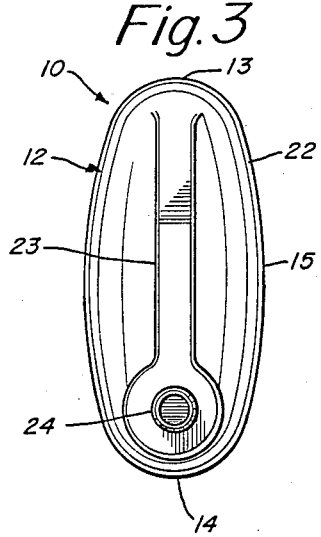
FIG. 1 is a side plan view of a first embodiment of the intra-labia urinary collection device of his invention for use by an adult.

A first embodiment of the "clean-catch," intra-labia urinary collection device of this invention adapted for use by an adult female is shown in FIGS. 1-6. The device is a hollow body 10 having an upper receiving end 11 and a lower discharge end 12. The body is formed from an upper portion 16 and a lower portion 17 joined at the perimeter by overlapping edges 18, 19 (FIG. 5), which may be joined by ultrasonic welding or an adhesive. The upper and lower portions 16, 17 are molded of a rigid plastic such as medium impact polystyrene. Alternatively, they may be formed of a soft rubber such as silicone. As a further alternative, the upper portion 16 may be molded of a soft rubber for comfort and the lower portion 17 of a rigid plastic or support.

Figure 2:
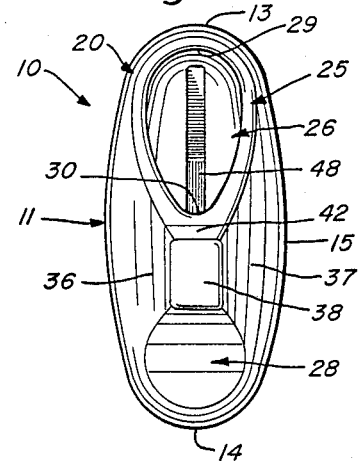
FIGS. 2 and 3 are plan views of the top (receiving) and bottom (discharge) ends, respectively, of the collection device of FIG. 1.
Figure 3:
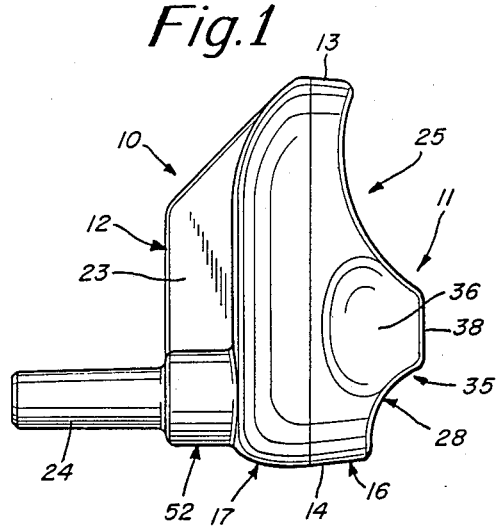

As shown in FIGS. 1, 2 and 6, the body 10 includes, from top to bottom, a curved upper wall 20 including recesses 25, 28, 36, 37 and an opening 26, vertical sidewalls 21, and a curved lower wall 22 including ridge 23, funnel 52, and spigot 24. The body is substantially oval (i.e., elliptical) in horizontal cross section taken at the vertical sidewalls 21, having narrower and rounded front and rear ends 13, 14, respectively, and a wider middle section 15 (FIG. 3).

The upper wall 20 includes a front concave recess 25 having an oval opening 26, a closed rear concave recess 28, closed concave recesses 36 and 37 on opposing sides of the device and a raised central plateau 38 (FIG. 2). The lower wall 22 includes a lengthwise ridge 23 which serves as a finger grip plate and a downwardly extending spigot 24 (FIG. 6). The interior of the body forms a hollow cavity or chamber 39 between sidewalls 21 for collecting urine (FIG. 6).

The upper receiving end 11 of the device is shown in FIG. 2. The front concave recess 25 extends about one-half the length of the upper wall. The oval opening 26, having a wider front portion 29 and a narrower rear portion 30, so as to be somewhat "pear-shaped", extends substantially the full length of the front recess 25, except for a closed vertical upper portion 42 adjacent the central plateau 38. A downwardly extending rounded lip 33 is provided around the oval opening 26 to act as a splash guard.

Figure 4:
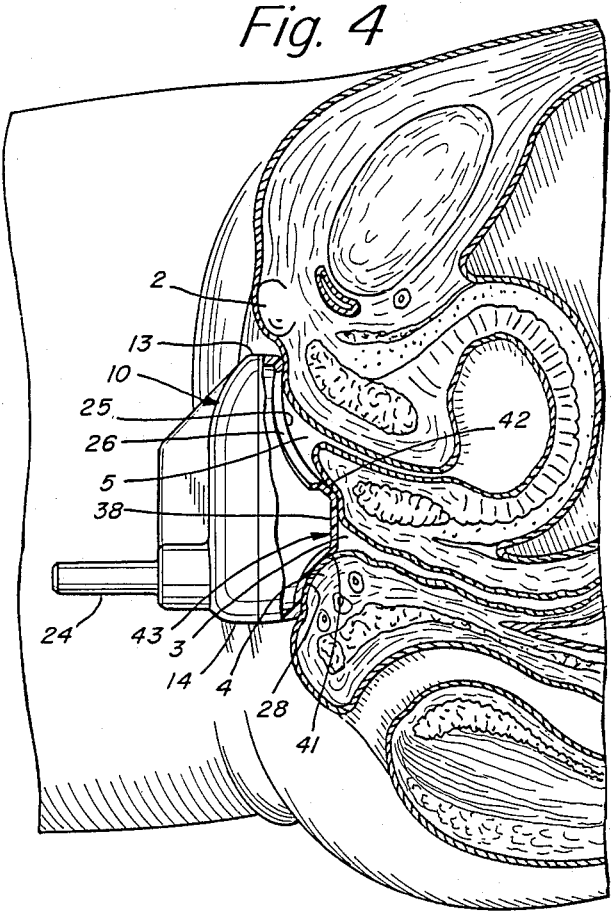
FIG. 4 shows the collection device externally applied at the external genitalia of an adult female in a supine position

The oval opening 26 and front recess 25 are sized and configured to fit between the labia minora folds distally of the clitoris 2 and forwardly of the vaginal opening 3 for receiving urine as it is discharged from the urethral opening 5 (FIG. 4). In the device shown, the front recess has a radius of 1.0" and is 1.25" in length. The oval opening is 1.040" in length and 0.625" in width at its widest point.

The rear half of the upper wall 20 includes the central plateau 38, side concave recesses 36 and 37, and the rear concave recess 28. Upper portions 39, 40 of side recesses 36, 37, upper portion 41 of rear recess 28, and closed upper portion 42 of front recess 25, form vertical sidewalls which support horizontal plateau 38. The closed rectangular projection 43 formed by plateau 38 and sidewalls 39, 40, 41, 42 is dimensioned and positioned to fit within the vaginal orifice 5 and seal the same to prevent fluids, cells and bacteria from the vaginal opening from contaminating the urine collected in the body (FIG. 4). In the device shown, the plateau is about 0.5625" in length and 0.375" in width, and the sidewalls extend 0.480" in height above the front end 13 of the body.

The rear concave recess 28 extends downwardly from plateau 38 to the rear end 14 of the body. The rear recess is closed and is sized and configured to seal against the vestibular tissue located adjacent and rearwardly of the vaginal opening. It seals the projection 43 within the vaginal opening 3 and prevents contamination of the urine collected in the body (FIG. 4). In the device shown, the rear recess has a radius of 0.500" and is 0.350" in height as measured from plateau 38, 0.750" in length, and 0.625" in width at its widest point.

The lower wall 22 includes a downwardly extending ledge 23 formed by a pair of parallel vertical sidewalls which function as a finger grip (FIG. 6). This enables the device to be easily placed by a person applying it to herself or by another applying it to the patient. An interior groove 48 down the center of ledge 23 channels urine into a funnel 52 formed at the rear end 53 of the lower wall. The circular funnel channels urine into a downwardly extending spigot 24 for draining the urine into a depository A lower vertical section of the upper body portion 16 and an upper vertical section of the lower body portion 17 are joined to form the vertical sidewalls 21 which extend around the entire perimeter of the device at its widest portion. These vertical sidewalls 21 form an enlarged chamber for the collection of urine. In the device shown, the chamber is 2.25" in length, 0.906" in width at its widest point, and 1.062" in depth. This provides a large volume area for collecting urine, which along with the enlarged circular funnel 52 disposed at the upper end of the spigot 24 and the interior groove 48 in ridge 23, enables the device to handle a fast rate of urine discharge without leakage or spillage.

The operative position of the device against the female genitalia is shown in FIG. 4. The vertical sidewalls 21 are sealingly engaged by the labia minora. The front end 13 is positioned just behind the clitoris 2, and the rear end 14 is positioned behind the vaginal opening 3 against the vestibular tissue 4. This positions the projection 43 within the vaginal opening 3 and the urine-receiving opening 26 below the urethral opening 5. The combination of the vertical sidewalls 21, side concave recesses 36, 37, rear recess 28 and central plateau 38 provide a superior sealing of the device to the external female genital tissue to prevent contamination of the urine sample by fluids, bacteria or cells from the vagina or anus. The enlarged hollow chamber 99 collects the urine without leakage and funnels it to the spigot. The splash guard around the oval opening prevents leakage as well.

In use, the patient first wipes the external female genitals to cleanse the same. The user then places the device in position, holding it there by positioning the forefinger and middle finger along opposing sides of the ridge 23. She then urinates into the device an collects the urine draining from the spigot 24 into a separate container (not shown) held in the other hand.

Figure 9:
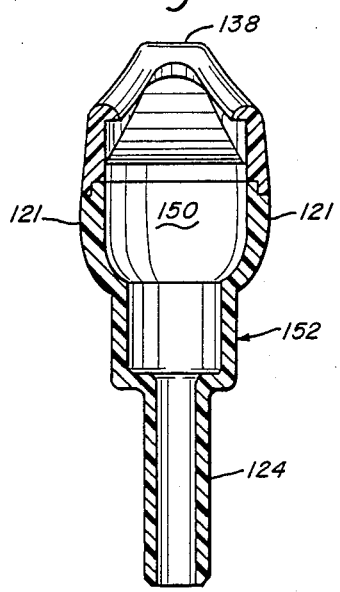
FIG. 9 is an end sectional view taken along the section lines 9—9 in FIG. 8.

A second pediatric version of the clean-catch urinary collection device is shown in FIGS. 7-9. The device is substantially similar to that shown in FIGS. 1-6 except that the upper body portion 16 has been rotated 180° and the oval opening 26 is in the smaller concave recess. This provides a better anatomic fit for a child.

Upper body portion 116 includes front recess 125 (of same dimensions as rear recess 28 in FIG. 2), central plateau 138, side recesses 136, 137 and rear recess 128 (of the same dimensions as front recess 25 in FIG. 2). The body extends between front end 113 and rear end 114. Lower body portion 117 includes vertical sidewalls 121 which form interior chamber 139, finger plate 123, rear funnel 152, and spigot 124. The device is positioned against the child's anatomy in a manner similar to FIG. 4 with front end 113 behind the clitoris, oval opening 126 beneath the urethral opening, plateau 138 within the vaginal opening, and rear recess 128 against the vestibular tissue behind the vaginal opening.

Although certain preferred embodiments of the invention have hereinbefore been described, it will be appreciated that variations of the invention will be perceived by those skilled in the art, which variations are nevertheless within the scope of this invention as defined by the claims appended hereto.

What is claimed is:

1. A "clean-catch," intra-labia urinary collection device comprising:
   a hollow body having an upper receiving end, a lower discharge end, and substantially vertical sidewalls forming an interior cavity, said body being substantially oval in horizontal cross section with narrowed front and rear ends and a wider middle section, said body being sized to be substantially enfolded within the labia minora with the front end positionable just behind the clitoris and the rear end behind the vaginal opening;

said upper receiving end having four outer concave recesses at the front, rear and two sides, respectively, which meet at a central elevated plateau;

said front concave recess extending about half the length of the body between the front and rear ends, said front recess having an opening extending substantially the length of the front recess and positioned to receive a urine stream directly from the urethral opening for collection in the cavity;

said central plateau and each adjacent portion of the front, rear and two side concave recesses being closed and forming a projection positionable within the vaginal opening to seal the same and prevent vaginal cells or bacteria from entering the cavity and contaminating urine being collected therein;

said rear concave recess being closed and positionable against the vestibular tissue behind the vaginal opening for maintaining the central plateau in sealing engagement within the vaginal opening;

a discharge spigot extending from the discharge end of the body for draining urine from the cavity into a depository; and a ridge in the lower discharge end running lengthwise between the front and rear ends having an interior groove for channeling urine directly into the discharge spigot.

2. The device of claim 1, wherein the central plateau is the uppermost portion of the device.

3. The device of claim 2, wherein the central plateau is substantially flat and rectangular.

4. The device of claim 1, wherein the opening has a lip which prevents urine from splashing out of the cavity.

5. The device of claim 1, wherein the central plateau extends about one quarter the length of the device and the rear recess extends about one quarter the length of the device.

6. The device of claim 1, wherein the rear recess is less deep than the front recess.

7. The device of claim 1, wherein the ridge is positionable between the middle finger and forefinger for holding the body in position against the female anatomy.

8. The device of claim 1, wherein, with respect to the total vertical height of the body not including the spigot, each of the central plateau, vertical sidewalls, and lower ridge comprise about one-third of the total height.

9. The device of claim 1, wherein the discharge spigot is disposed adjacent the rear end of the device.

10. An intra-labia urinary collection device comprising:

substantially vertical sidewalls defining an interior chamber, said body being substantially oval in horizontal cross section with rounded front and rear ends and its widest portion at midsection, and said body being sized and configured to be substantially enfolded by the labia minora of the user;

the upper wall of said body including, from front to back, a front concave recess, a projection, and a rear concave recess, the front concave recess extending about half the length of the body between the front and rear ends;

an opening extending substantially the length of the front concave recess, said opening being sized and positioned to receive a urine stream directly from the urethral opening;

said projection extending upwardly from the front recess and having a closed and flattened upper surface and closed sidewalls completely surrounding the same and being positionable to seal the vaginal opening and prevent vaginal fluids from entering the chamber;

said rear concave recess being closed and positionable against the vestibular tissue rearwardly of the vaginal opening for preventing contamination of the urethral fluid collected in the chamber and for sealing the projection within the vaginal opening;

a spigot extending downwardly from the lower wall of said body at the rear end of the body for draining fluids away from said chamber; and a ridge in the lower wall running lengthwise between the front and rear ends having an interior groove for channeling urine directly into the spigot.

* * * * *

UNITED STATES PATENT AND TRADEMARK OFFICE
CERTIFICATE OF CORRECTION

PATENT NO. : 4,911,698

DATED : March 27, 1990

INVENTOR(S) : Wapner

It is certified that error appears in the above-identified patent and that said Letters Patent is hereby corrected as shown below:

Column 3, line 10, Change "39" to -- 50 --.

Column 4, line 23, Change "99" to -- 50 --.

Column 4, line 46, Change "139" to -- 150 --.

Column 6, line 12, Before "substantially" insert -- a hollow body having an upper wall, a lower wall, and --.

Signed and Sealed this

Ninth Day of July, 1991

*Attest:*

HARRY F. MANBECK, JR.

*Attesting Officer*  Commissioner of Patents and Trademarks